(12) United States Patent
Beerwerth et al.

(10) Patent No.: US 11,389,982 B2
(45) Date of Patent: Jul. 19, 2022

(54) SKIN TREATMENT PERSONAL CARE DEVICE AND METHOD OF MANUFACTURE

(71) Applicant: The Gillette Company LLC, Boston, MA (US)

(72) Inventors: Frank Beerwerth, Kaltenholzhausen (DE); Judith VonDahlen, Frankfurt (DE); Dalibor Dadic, Koenigstein (DE)

(73) Assignee: The Gillette Company LLC, Boston, MA (US)

( * ) Notice: Subject to any disclaimer, the term of this patent is extended or adjusted under 35 U.S.C. 154(b) by 173 days.

(21) Appl. No.: 16/841,435

(22) Filed: Apr. 6, 2020

(65) Prior Publication Data

US 2020/0316800 A1 Oct. 8, 2020

Related U.S. Application Data

(60) Provisional application No. 62/829,795, filed on Apr. 5, 2019.

(51) Int. Cl.
*B26B 21/46* (2006.01)
*A61N 5/06* (2006.01)
(Continued)

(52) U.S. Cl.
CPC ............ *B26B 21/46* (2013.01); *A61N 5/0616* (2013.01); *A61N 5/0624* (2013.01); *B26B 21/4012* (2013.01); *B26B 21/4056* (2013.01); *B26B 21/526* (2013.01); *H05K 1/181* (2013.01); *H05K 3/303* (2013.01); *H05K 7/2039* (2013.01); *A61N 2005/0626* (2013.01);
(Continued)

(58) Field of Classification Search
CPC . B26B 21/46; B26B 21/4012; B26B 21/4056; B26B 21/526; A61N 5/0616; A61N 5/0624; A61N 2005/0626; A61N 2005/0644; A61N 2005/0652; A61N 2005/0668; H05K 1/181; H05K 3/303; H05K 2201/10106; H05K 2201/10151; H05K 2201/10522
See application file for complete search history.

(56) References Cited

U.S. PATENT DOCUMENTS 5,820,625 A 10/1998 Izawa
7,291,140 B2 11/2007 Macfarland
(Continued)

FOREIGN PATENT DOCUMENTS

CN 2848495 Y 12/2006
CN 203712742 U 7/2014
(Continued)

OTHER PUBLICATIONS

International Search Report dated Jul. 10, 2020, 19 pages.

*Primary Examiner* — Omar Flores Sanchez
(74) *Attorney, Agent, or Firm* — John M. Lipchitz

(57) ABSTRACT

A skin treatment personal care with a handle having a gripping portion at one end and a head portion at an opposing end. The head portion includes a heat dissipating housing having a top surface and defines a pocket. The heat dissipating housing is made of a material having a thermal diffusivity greater than 10 W/m K. A light emitting diode adapted to provide one or more skin benefits is positioned within in the pocket. A window forms a water tight seal covering the LED.

13 Claims, 5 Drawing Sheets

(51) Int. Cl.
*B26B 21/40* (2006.01)
*B26B 21/52* (2006.01)
*H05K 1/18* (2006.01)
*H05K 3/30* (2006.01)
*H05K 7/20* (2006.01)

(52) U.S. Cl.
CPC ............... *A61N 2005/0644* (2013.01); *A61N 2005/0652* (2013.01); *A61N 2005/0668* (2013.01); *H05K 2201/10106* (2013.01); *H05K 2201/10151* (2013.01); *H05K 2201/10522* (2013.01)

(56) References Cited

U.S. PATENT DOCUMENTS

| | | |
|---|---|---|
| 7,452,356 B2 | 11/2008 | Grove |
| 8,516,706 B2 | 8/2013 | Flyash |
| 10,894,330 B2* | 1/2021 | Goeder ............... B26B 21/4056 |
| 2004/0054386 A1 | 3/2004 | Martin |
| 2008/0134511 A1 | 6/2008 | Salvatore |
| 2009/0255123 A1* | 10/2009 | Tomassetti .............. B26B 21/48 |
| | | 30/34.05 |
| 2010/0069898 A1 | 3/2010 | Oneil |
| 2013/0344454 A1 | 12/2013 | Nath |
| 2014/0315142 A1* | 10/2014 | Montgomery ....... A61N 5/0624 |
| | | 433/29 |
| 2015/0045843 A1 | 2/2015 | Asah |
| 2015/0282878 A1 | 10/2015 | Kindermann |
| 2017/0056686 A1 | 3/2017 | Gamelin |
| 2017/0370992 A1* | 12/2017 | Heubach .............. G01R 31/327 |
| 2019/0167400 A1* | 6/2019 | Barnes ............... A46B 15/0034 |

FOREIGN PATENT DOCUMENTS

| | | |
|---|---|---|
| EP | 2753261 B1 | 12/2018 |
| JP | 2001029124 A | 2/2001 |

* cited by examiner

SKIN TREATMENT PERSONAL CARE DEVICE AND METHOD OF MANUFACTURE

FIELD OF THE INVENTION

The present invention relates to shaving razors and more particularly more specifically to safety razors for wet shaving that incorporate a light energy source that provides a beneficial effect to the skin of the user.

BACKGROUND OF THE INVENTION

The onset of facial hair growth typically begins during puberty along with acne. Some consumers avoid shaving because of the difficulties and concerns with shaving acne prone skin, especially with wet shaving razors. The use of light energy to promote healing and skin treatment such as photo rejuvenation and so-called anti-aging is known. Several commercial devices including the WARP 10 marketed by WARP THERAPY; the DERMASTYLE SKIN REJUVENATOR marketed by LUMIPORT; the LED SKIN PHOTO REJUVENATION LIGHT marketed by LIGHT THERAPY PRODUCTS and devices marketed by OMNILUX utilize light emitting diodes (LEDs) of diverse wavelengths for different effects. Blue light in the approximate range of 400-500 nanometer (nm) wavelength spectrum has been effective in treating acne and can be microbicidal. For example, Positively Clear Acne Clearing Blue Light by TRIA BEAUTY®. Visible and near infra-red red light in the approximate range of 600-900 nm wavelength spectrum has proved helpful in wound care and the reduction of wrinkles and age spots. An important aspect of these light energy devices is that the power output is less than that of devices used for hair removal, for example, U.S. Pat. No. 5,735,844 to Anderson et al being representative of disclosing light energy devices for hair removal and hair growth inhibition.

Shaving razors have been proposed that incorporate a light energy source that provides a beneficial effect to the skin of the user in a shaving razor. However, the size of the shaving razor cartridge is relatively small. Accordingly, the light energy source may generate heat that the shaving razor cartridge is unable to dissipate and/or control in a safe and efficient manner. In addition, the light energy source may be harmful if it is inadvertently exposed to the eyes. The application of light energy during a shaving stroke creates other issues, such as higher power LED may be used to compensate for the relatively small footprint of the razor as well as short contact time (e.g., time during a single shaving stroke). Accordingly, there is a need to provide a shaving razor capable of delivering safe and reliable light energy without burning the skin.

SUMMARY OF THE INVENTION

The invention features, in general, a simple, efficient skin treatment personal care with a handle having a gripping portion at one end and a head portion at an opposing end. The head portion includes a heat dissipating housing having a top surface and defines a pocket. The heat dissipating housing is made of a material having a thermal diffusivity greater than 10 W/m K. A light emitting diode adapted to provide one or more skin benefits is positioned within the pocket. A window forms a water tight seal covering the LED.

In another aspect, the invention features, in general, a simple, efficient light bar assembly having a chassis having a top surface and a front wall. A printed circuit board is mounted to the chassis. A light emitting diode adapted to provide one or more skin benefits is mounted to the printed circuit board. A heat dissipating housing is mounted over the printed circuit board. The heat dissipating housing has a top surface that defines a pocket. The heat dissipating housing includes a material having a thermal diffusivity greater than 10 W/m K. The light emitting diode is positioned within the pocket and a window forms a water tight seal covering the LED.

In another aspect, the invention features, in general, a simple, efficient method of assembling a skin treatment personal care device by mounting a printed circuit board to a chassis having a top surface and a front wall. A light emitting diode adapted to provide one or more skin benefits is mounted to the printed circuit board. A heat dissipating housing having a material with a thermal conductivity greater than 10 W/m K is mounted over the printed circuit board. The light emitting diode is positioned within a pocket of the heat dissipating housing. The light emitting diode is covered with a window. A water tight between the window and the heat dissipating housing is formed.

The details of one or more embodiments of the invention are set forth in the accompanying drawings and the description below. It is understood that certain embodiments may combine elements or components of the invention, which are disclosed in general, but not expressly exemplified or claimed in combination, unless otherwise stated herein. Other features and advantages of the invention will be apparent from the description and drawings, and from the claims.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings.

DETAILED DESCRIPTION OF THE INVENTION

Figure 1A:
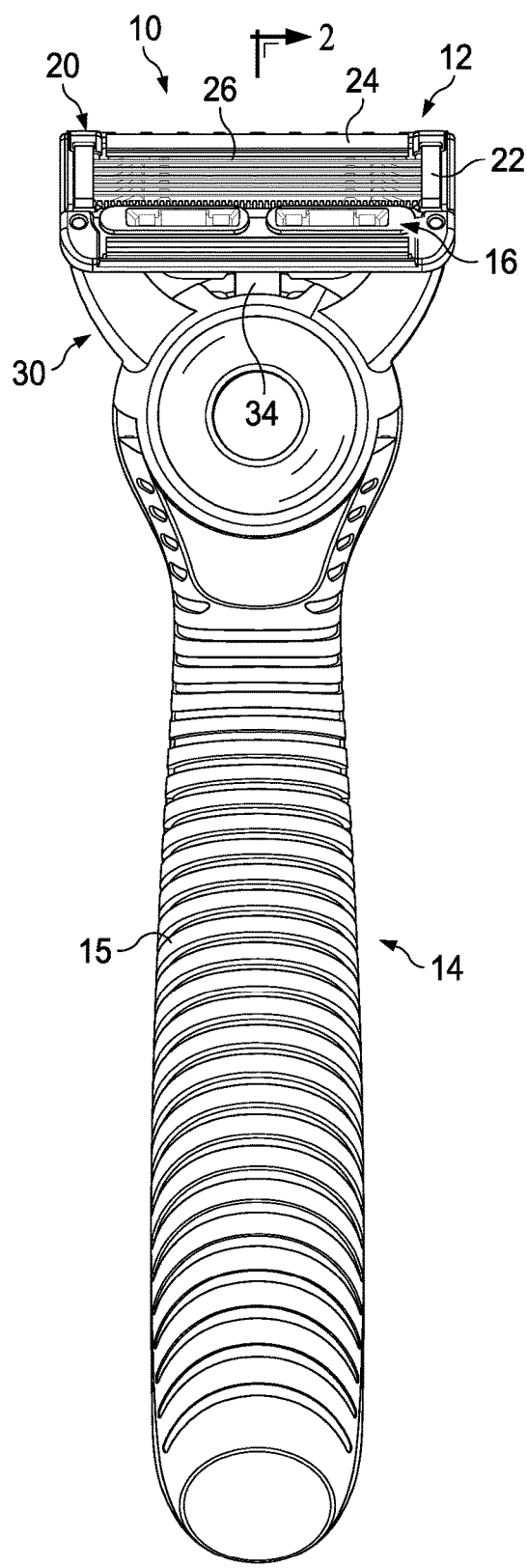
FIG. 1A is a front view of one possible embodiment of a skin treatment personal care device.
Figure 1B:
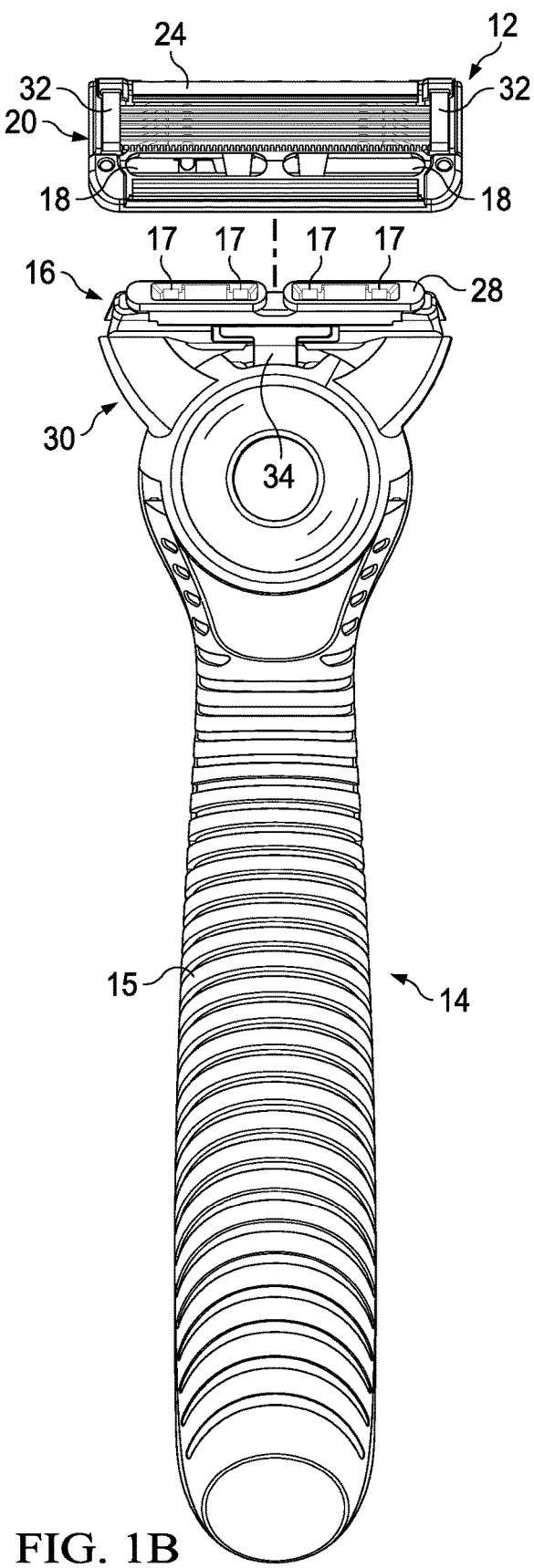
FIG. 1B is a front view of the skin treatment personal care device with a shaving razor cartridge detached from a handle.

Referring to FIGS. 1A and 1B, one possible embodiment of the present disclosure is shown illustrating a skin treatment personal care device 10, such as a shaving razor. In certain embodiments, the skin treatment personal care device 10 may include a shaving razor cartridge 12 mounted to a handle 14, as shown in FIG. 1A. However, it is understood other treatment heads may alternatively be mounted to the handle 14, such as, a toothbrush or an applicator. The shaving razor cartridge 12 may be fixedly or pivotably mounted to the handle 14. The handle 14 may include a gripping portion 15 that holds a power source, such as one or more batteries (not shown) that supply power to a light bar assembly 16. In certain embodiments, the light bar assembly 16 may comprise one or more light emitting diodes (LEDS) 17. The LED (or LEDs) are positioned to face the skin of the user when the light bar assembly 16 is mounted to the shaving razor cartridge 12 and the user takes a shaving stroke. For example, the light bar assembly 16 may extend into one or more openings 18 (FIG. 1B) defined by a housing 20 of the shaving razor cartridge 12.

The light energy emitted by the LED has at least one wavelength in the range 400-1000 nm. At least one wavelength in the range 400-700 nm has also been found to be beneficial. Each LED may have a power consumption more than 100 mW, more preferably more than 200 mW, and a radiant power more than 100 mW, more preferably more than 200 mW. The light energy emitted by the LED provides at least one of acne treatment; bactericidal effects; repair of photodamage; anti-aging effects; reduction of scarring and wound healing, including healing wounds or other skin damage caused by shaving.

The shaving razor cartridge 12 may be permanently attached or removably mounted from the handle 14, thus allowing the shaving razor cartridge 12 to be replaced. FIG. 1B illustrates the shaving razor cartridge 12 removed from the handle 14. The housing 20 of the shaving razor cartridge 12 may have include a guard 22, a cap 24 and one or more blades 26 mounted to the housing 20 between the cap 24 and the guard 22. The guard 22 may be toward a front portion of the housing 20 and the cap 24 may be toward a rear portion of the housing 20 (i.e., the guard 22 is in front of the blades 26 and the cap 24 is behind the blades 26). The guard 22 and the cap 24 may define a shaving plane that is tangent to the guard 22 and the cap 24. The guard 22 may be a solid or segmented bar that extends generally parallel to the blades 26. In certain embodiments, the light bar assembly 16 may be positioned in front of the guard 22. However, it is understood the light bar assembly may be positioned anywhere on the housing 20 (e.g., at the rear of the housing 20, near the cap 20). The light bar assembly 16 may comprise an outer surface 28 that contacts a consumer's skin during a shaving stroke. The light bar assembly 16 may be mounted to a head portion 30 of the handle 14. The light emitting diodes 17 may be recessed within the light bar assembly 16 (e.g., spaced apart from the outer surface 28).

In certain embodiments, the blades 26 may be mounted to the housing 20 and secured by one or more clips 32. Other assembly methods known to those skilled in the art may also be used to secure and/or mount the blades 26 to the housing 20 including, but not limited to, wire wrapping, cold forming, hot staking, insert molding, ultrasonic welding, and adhesives. The clips 32 may comprise a metal, such as aluminum for conducting heat and acting as a sacrificial anode to help prevent corrosion of the blades 26. Although five blades 26 are shown, the housing 20 may have more or fewer blades 26 depending on the desired performance and cost of the shaving razor cartridge 12.

In certain embodiments, it may be desirable to provide light in front of the blades 26. For example, the light bar assembly 16 may be positioned in front of the guard 20 and/or the skin engaging member 26. As will be described in greater detail below, the light bar assembly 16 may be mounted to the housing 20 and in communication with the power source (not shown) via a printed circuit board (PCB) 34. In certain embodiments, the printed circuit board (PCB) 34 may be flexible to facilitate movement of the shaving razor cartridge 12. The light emitting diodes 17 may be mounted to the printed circuit board 34 and operatively coupled to the power source.

The cap 24 may be a separate molded (e.g., a shaving aid filled reservoir) or extruded component (e.g., an extruded lubrication strip) that is mounted to the housing 20. In certain embodiments, the cap 24 may be a plastic or metal bar to support the skin and define the shaving plane. The cap 24 may be molded or extruded from the same material as the housing 20 or may be molded or extruded from a more lubricious shaving aid composite that has one or more water-leachable shaving aid materials to provide increased comfort during shaving. The shaving aid composite may comprise a water-insoluble polymer and a skin-lubricating water-soluble polymer. Suitable water-insoluble polymers which may be used include, but are not limited to, polyethylene, polypropylene, polystyrene, butadiene-styrene copolymer (e.g., medium and high impact polystyrene), polyacetal, acrylonitrile-butadiene-styrene copolymer, ethylene vinyl acetate copolymer and blends such as polypropylene/polystyrene blend, may have a high impact polystyrene (i.e., Polystyrene-butadiene), such as Mobil 4324 (Mobil Corporation).

Suitable skin lubricating water-soluble polymers may include polyethylene oxide, polyvinyl pyrrolidone, polyacrylamide, hydroxypropyl cellulose, polyvinyl imidazoline, and polyhydroxyethylmethacrylate. Other water-soluble polymers may include the polyethylene oxides generally known as POLYOX (available from Union Carbide Corporation) or ALKOX (available from Meisei Chemical Works, Kyota, Japan). These polyethylene oxides may have molecular weights of about 100,000 to 6 million, for example, about 300,000 to 5 million. The polyethylene oxide may comprise a blend of about 40 to 80% of polyethylene oxide having an average molecular weight of about 5 million (e.g., POLYOX COAGULANT) and about 60 to 20% of polyethylene oxide having an average molecular weight of about 300,000 (e.g., POLYOX WSR-N-750). The polyethylene oxide blend may also contain up to about 10% by weight of a low molecular weight (i.e., MW<10,000) polyethylene glycol such as PEG-100.

The shaving aid composite may also optionally include an inclusion complex of a skin-soothing agent with a cylcodextrin, low molecular weight water-soluble release enhancing agents such as polyethylene glycol (e.g., 1-10% by weight), water-swellable release enhancing agents such as cross-linked polyacrylics (e.g., 2-7% by weight), colorants, antioxidants, preservatives, microbicidal agents, beard softeners, astringents, depilatories, medicinal agents, conditioning agents, moisturizers, cooling agents, etc.

Figure 2:
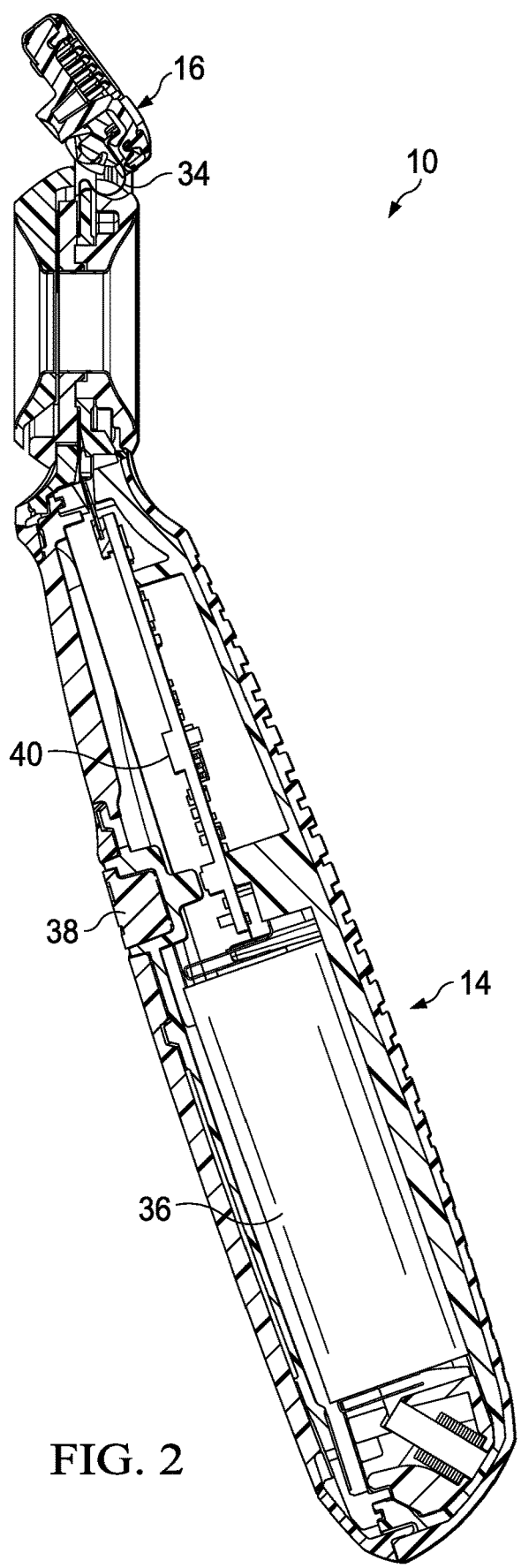
FIG. 2 is a cross section view of the skin treatment personal care device, taken generally along the line 2-2 of FIG. 1A.

Referring to FIG. 2, a cross section view of the skin treatment personal care device is shown, taken generally along the line 2-2—of FIG. 1A. The handle 14 may hold a battery 36 to supply power to the light bar assembly 16. A power switch 38 (e.g., a button) may be provided on the handle 14 to turn power on and off to the light bar assembly 16. In certain embodiments, the power switch 38 may be illuminated to indicate the status of the light bar 16. The battery 36 may be operatively coupled to a control circuit 40 to regulate power to the light bar assembly 16. As will be explained in greater detail below, the control circuit may turn off power to the light bar assembly 16 if the temperature of the light bar assembly 16 exceeds a first predetermined temperature. In certain embodiments, the first temperature may be approximately 50 degrees Celsius, for example, about 42 degrees Celsius to 52 degrees Celsius. The control circuit 40 may also switch power back to the light bar assembly 16 once the temperature of the light bar assembly falls back below a second predetermined temperature, which may be less than the first predetermined temperature. In certain embodiments, the second temperate may be about 43 degrees Celsius to about 45 degrees Celsius. In other embodiments, the control circuit 40 may only switch the power on if the temperature sensed is less than the first predetermined temperature.

Figure 3:
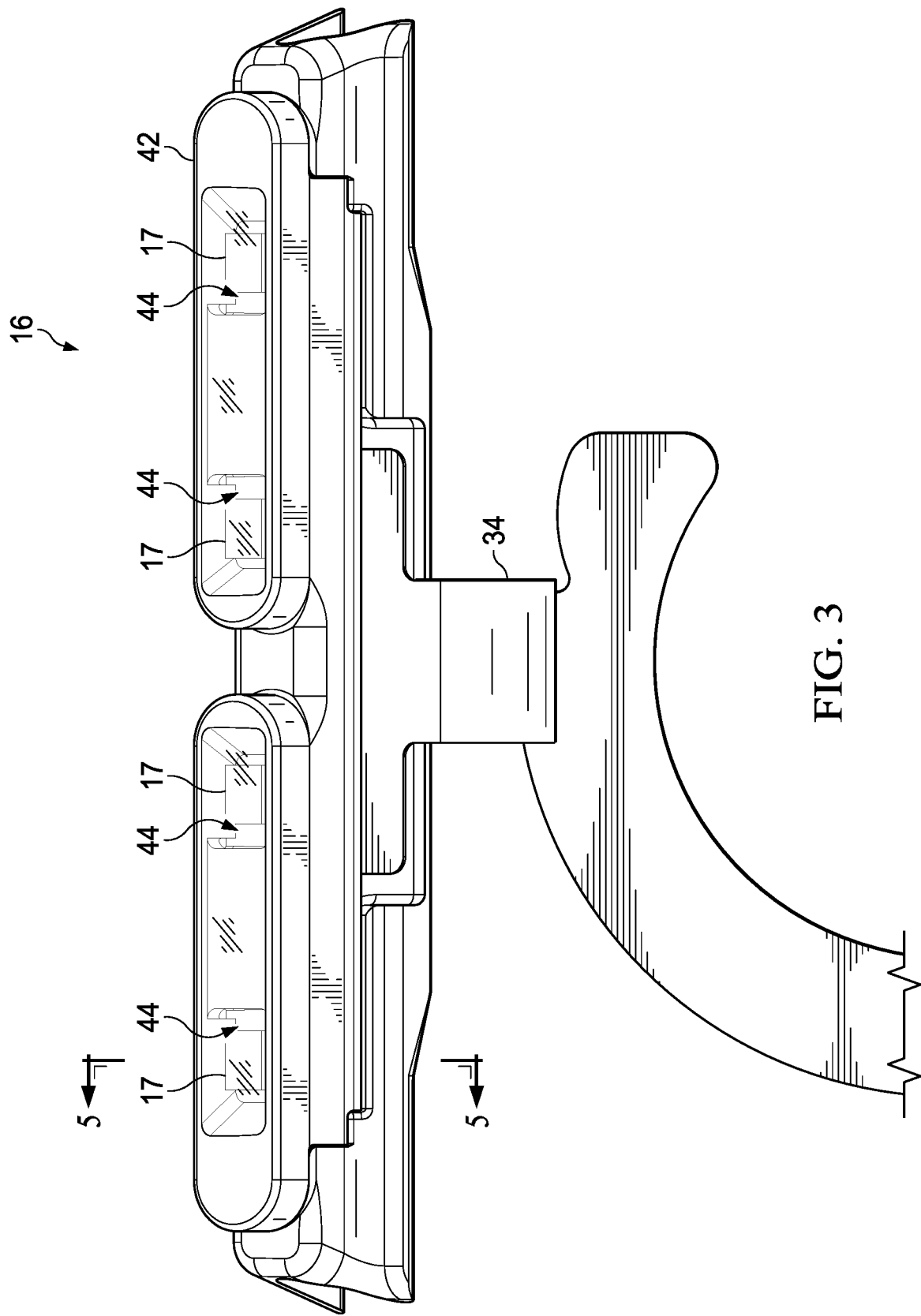
FIG. 3 is a perspective view of one possible embodiment of a light bar.
Figure 4:
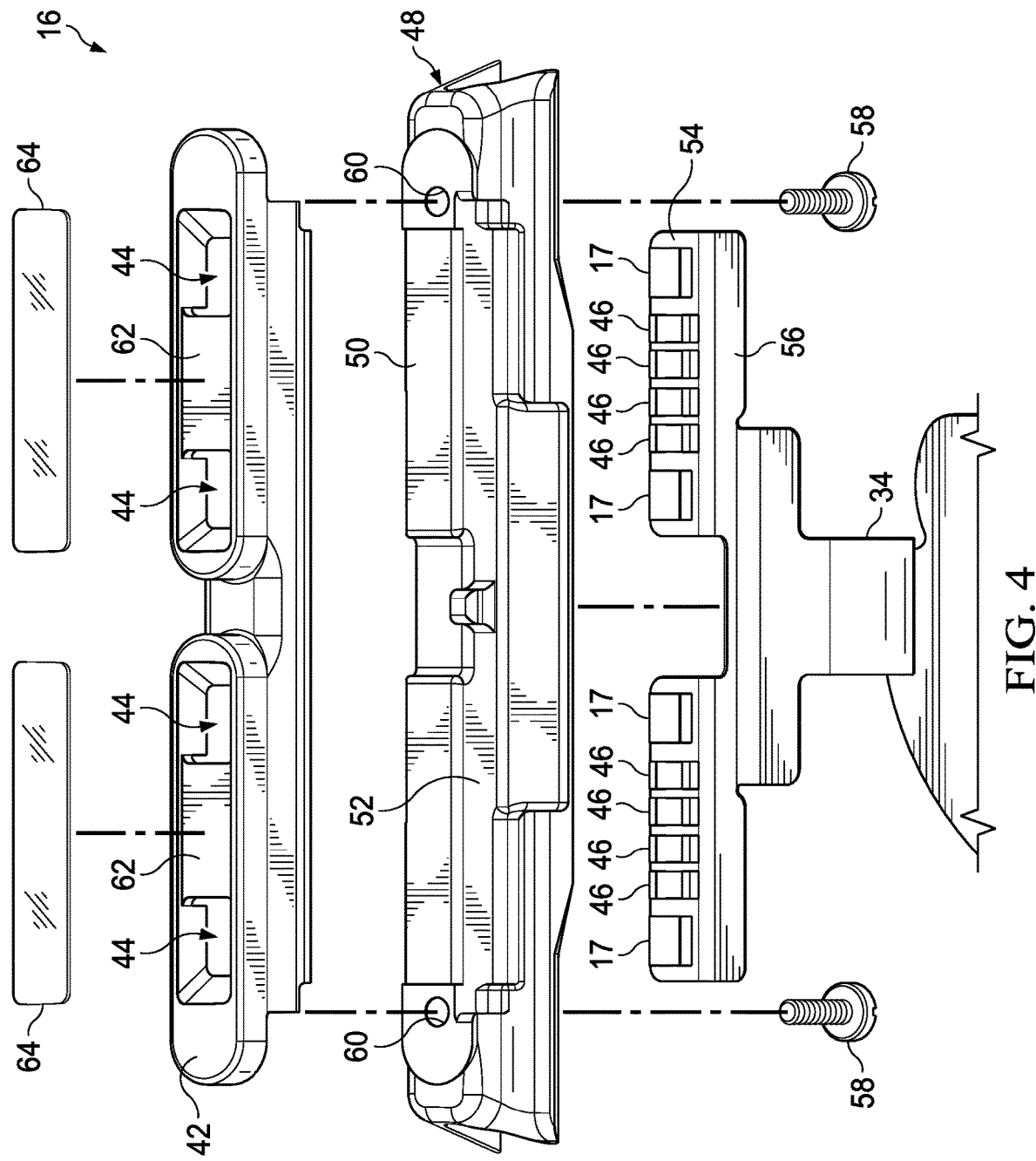
FIG. 4 is an assembly view of the light bar of FIG. 3

Referring to FIGS. 3 and 4, a perspective view and an assembly view of the light bar assembly 16 is illustrated. The light bar assembly 16 may include a heat dissipating housing 42 defining one or more pockets 44. The light emitting diode 17 may be positioned with the pocket(s) 44. A considerable amount of heat may be produced by the light emitting diodes 17, which can result in discomfort, pain or potential injury to a user. As will be explained in greater detail below, the light bar assembly 16 may include one or more thermal sensors 46 that send a signal to the control circuit 40 (FIG. 2) to turn off power to the light emitting diodes 17 if a predetermined threshold temperature is reached to prevent burning the skin of a user. Thermal sensors provide a good safety mechanism for light emitting diode(s) 17, but turning power off or reducing power to the light emitting diode(s) 17 may cause the skin treatment personal care device to be inefficient. For example, if the power to the light emitting diode(s) is constantly switched off and on during use, the light emitting diode(s) may not transmit a sufficient amount of energy to result in the desired skin benefit. To keep the light emitting diodes 17 switched on as much as possible during use, i.e. without the light bar assembly 16 heating up beyond the first predetermined temperature, it may be desirable to dissipate as much of the heat generated by the LEDs 17 to the surrounding area. During use of the skin treatment the personal care device 10, the largest heat sink that is coupled through close contact to the light bar assembly 16 is typically the skin of the user. Therefore it may be desirable to provide a construction and selection of materials for the light bar assembly 16 that enables rapid transport of heat from the LEDs 17 to the user's skin. In certain embodiments, the heat dissipating housing 42 of the light bar assembly 16 comprising a material having a thermal conductivity greater than 10 W/m K. This may facilitate a high rate of transfer of heat from the hot end (the LED contacting side) to the cold end (the skin contacting side). Examples of materials that have sufficient thermal conductivity may include, but are not limited to aluminum, copper, steel, or thermally conducting polymers such as Coolpoly E8101. Below are listed examples of various materials with respective thermal conductivity.

| Material | Thermal conductivity k (W/m K) |
|---|---|
| Copper | 413 |
| Aluminium | 237 |
| Sapphire glass | 24 |
| Coolpoly E8101 | 15 |
| Steel 304 | 15 |
| Glass | 1 |
| Nylon-6 | 0.25 |
| Polyethylene | 0.1 |

Referring to FIG. 4, an assembly view of the light bar assembly 16 is illustrated. The light emitting diode(s) 17 may be mounted to and in electrical communication with the printed circuit board 34. The thermal sensor(s) 46 may be mounted to and in electrical communication with the printed circuit board 34. The printed circuit board 34 may transfer power and/or electrical signals to and from the power source 36 (FIG. 2) and the control circuit 40 (FIG. 2) as well as to the light emitting diode(s) 17 and the thermal sensor(s) 46. In certain embodiments, the thermal sensor(s) 46 may be positioned between a pair of light emitting diodes 17 for improved accuracy. A plurality of thermal sensors 46 may be positioned between and adjacent to a pair of the thermal sensors 46 to facilitate more accurate temperature readings of the heat dissipating housing 42. For an additional level of safety, multiple thermal sensors 46 positioned between the light emitting diodes 17 may provide a level redundancy in case one or more of the thermal sensors 46 fail. If the sensor(s) 46 identify that the first predetermined temperature is reached, the control circuit 40 may turn power to the LED(s) 17 off, turn power to the LED(s) 17 from continuous to intermittent (e.g., so the LED(s) 17 blink), or reduce power to the LED(s).

The printed circuit board 34 may be mounted to a chassis 48. The chassis 48 may be manufactured from steel, aluminum, copper or polymeric material. The chassis 48 may have a top surface 50 and front surface 52. A top portion 54 of the printed circuit board 34 may be positioned on the top surface 50 of the chassis 48 and a front portion 56 of the printed circuit board 34 may be positioned against the front surface 52 of the chassis 48. In certain embodiments, adhesive may be used to secure the printed circuit board to the chassis 48. The positioning of the front portion 56 and the top portion 54 on the chassis 48 may facilitate the securing process (e.g., movement of the circuit board 34 is limited during securing). The thermal sensor(s) 46 and/or the light emitting diode(s) may be mounted to the top portion 54 of the printed circuit board 34 either before or after the printed circuit board 34 is secured to the chassis 48.

The printed circuit board 34 may be captured between the chassis 48 and the heat dissipating housing 42. The heat dissipating housing 42 may be mounted over the printed circuit board 34 and the chassis 48. In certain embodiments, the heat dissipating housing 42 may be mounted over both the top portion 54 and the front portion 56 of the printed circuit board 34. Similarly, the heat dissipating housing 42 may be mounted over both the top surface 50 and the front surface 52 of the chassis 48. One or more retaining member(s) 58 may extend through a respective opening(s) 60 in the chassis 48 and into the heat dissipating housing 42 to secure the chassis 48 to the heat dissipating housing 42. The pockets 44 of the heat dissipating housing 42 may be positioned around respective light emitting diodes 17. The heat dissipating housing 42 may have one or more sensor pads 62. The sensor pad(s) 62 may be positioned between a pair of pockets 44. In certain embodiments, the sensor pad(s) 62 may rest on top (e.g., in contact) of the thermal sensor(s) 46 to give an accurate temperature reading of the temperature of the heat dissipating housing 42. As will be described in greater detail below, one or more window(s) 64 may be mounted to the heat dissipating housing 42 to cover the pockets 44 and thus the light emitting diodes 17. The window(s) 64 may provide a water tight seal to prevent water ingress into the pockets 44.

The window(s) 64 may be translucent or transparent for the light emitted by the light emitting diodes 17 to reach the skin. The window(s) 64 may comprise glass, polycarbonate and other translucent or transparent polymers. In the case of certain transparent polymers, e.g. acrylate, silicone or epoxy, the polymer may be filled into the pockets while in a liquid state and then cured to form solid transparent or translucent window(s) 64. In certain embodiments, the window(s) 64 may comprises a transparent or translucent material that also aids the dissipation of heat to the skin, such as sapphire glass. Sapphire glass may be preferred over glass (e.g., silicon dioxide) because of its improved thermal properties to facilitate the dissipation of heat. In certain embodiments, the window(s) 64 may be have a thermal conductivity greater than about 10 W/m K.

Figure 5:
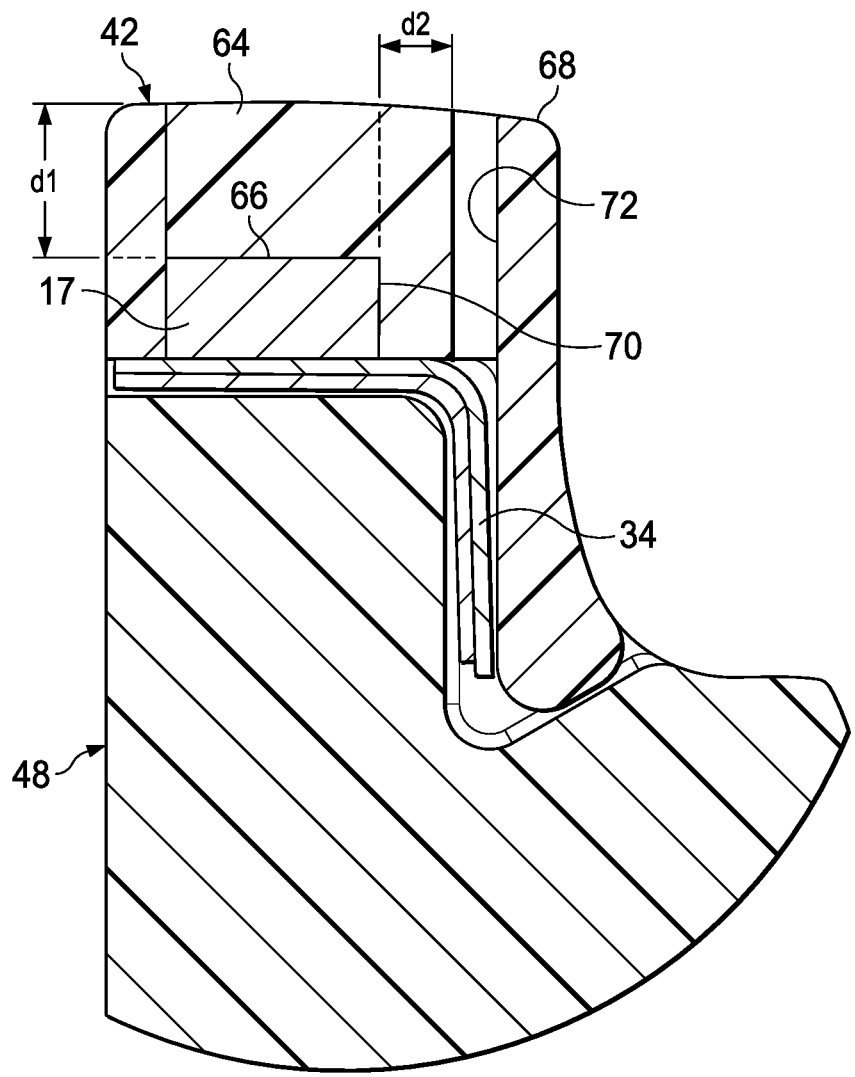
FIG. 5 is a cross section view of the light bar, taken generally along the line 5-5 of FIG. 3.

Referring to FIG. 5, a cross sectional view of the light bar assembly 16 is illustrated, taken generally along the line 5-5 of FIG. 3. As previously discussed, one or more of the light emitting diode(s) 17 may be positioned within one of the respective pocket(s) 44 of the heat dissipating housing 42. A top surface 66 of the light emitting diode(s) 17 may be recessed a distance of "d1" relative to a top surface 68 of the heat dissipating housing 42 to facilitate light beam formation. In certain embodiments, the distance d1 may be about 0.1 mm to about 1 mm. The distance "d1" may also represent a thickness of the window 64. One or more sides 70 of the light emitting diode(s) 17 may be positioned a distance d2 from an inner side wall 72 of the heat dissipating housing 42 to facilitate water sealing of the light emitting diode(s) 17. For example, d2 may be about 0.1 mm to about 1.0 mm. Accordingly, the window 64 may be positioned to face more than one side of the light emitting diode(s) 17. The window 64 may be secured to the heat dissipating housing 42 with a filler or an adhesive. Alternatively, the window 64 may comprise a transparent filler (e.g., an adhesive such as Epo-Tek 301, which is also safe to use in contact with skin, or silicone rubber). Accordingly, the transparent filler may allow for light to be transmitted through the window 64 to provide one or more skin benefits in addition to providing a water tight seal and facilitate the dissipation of heat from the light emitting diode(s) 17.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin treatment personal care device comprising:
   a handle having a gripping portion at one end and a head portion at an opposing end, the head portion includes a heat dissipating housing having a top surface and defining a pocket, the heat dissipating housing comprising a material having a thermal diffusivity greater than 10 W/m K;
   a light emitting diode adapted to provide one or more skin benefits positioned within in the pocket;
      a window forming a water tight seal covering the LED; and
      a shaving razor cartridge mounted to the heat dissipating housing.

2. The skin treatment personal care device of claim 1 wherein the LED is recessed by a vertical distance of 0.1 mm to 1 mm from top surface of the heat dissipating housing.

3. The skin treatment personal care device of claim 1 wherein the window comprises a transparent filler at least partially filling the pocket.

4. The skin treatment personal care device of claim 1 wherein the window comprises sapphire glass.

5. The skin treatment personal care device of claim 1 wherein heat dissipating housing comprises aluminum.

6. The skin treatment personal care device of claim 1 wherein the LED has a wavelength of 400 nm to 700 nm.

7. The skin treatment personal care device of claim 1 wherein the light emitting diode is mounted to a printed circuit board that is in communication with a control circuit.

8. The skin treatment personal care device of claim 7 further comprising a thermal sensor mounted to the printed circuit board that is in communication with the control circuit.

9. A light bar assembly comprising:
   a chassis having a top surface and a front wall;
   a printed circuit board mounted to the chassis;
   a light emitting diode adapted to provide one or more skin benefits mounted to the printed circuit board;
   a heat dissipating housing mounted over the printed circuit board, the heat dissipating housing having a top surface defining a pocket, the heat dissipating housing comprising a material having a thermal diffusivity greater than 10 W/m K, wherein the light emitting diode is positioned within the pocket and a window forming a water tight seal covers the LED, and a thermal sensor is mounted between a pair of light emitting diodes.

10. The light bar assembly of claim 9 further comprising a thermal sensor mounted to the circuit board.

11. The light bar assembly of claim 9 wherein the circuit board is mounted to the top surface of the chassis and the front wall of the chassis.

12. The light bar assembly of claim 9 further comprising a plurality of sensors positioned between the pair of light emitting diodes.

13. The light bar assembly of claim 9 wherein the light emitting diode is recessed a horizontal distance of 0.1 mm to 1 mm below the top surface of the heat dissipating housing.

* * * * *